(12) United States Patent
Viens et al.

(10) Patent No.: US 10,307,309 B2
(45) Date of Patent: Jun. 4, 2019

(54) CARDED STAPLE FIBER NONWOVENS

(71) Applicant: The Procter & Gamble Company, Cincinnati, OH (US)

(72) Inventors: Gerard A. Viens, Wyoming, OH (US); Stephen Lebeuf Hardie, Mason, OH (US); Edward Paul Carlin, Maineville, OH (US); Ronda Lynn Glassmeyer, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 675 days.

(21) Appl. No.: 14/731,802

(22) Filed: Jun. 5, 2015

(65) Prior Publication Data

US 2015/0351976 A1    Dec. 10, 2015

Related U.S. Application Data

(60) Provisional application No. 62/008,677, filed on Jun. 6, 2014.

(51) Int. Cl.
*A61F 13/15*    (2006.01)
*A61F 13/511*    (2006.01)
(Continued)

(52) U.S. Cl.
CPC ...... *A61F 13/51121* (2013.01); *A61F 13/537* (2013.01); *A61F 13/5376* (2013.01); *D04H 1/425* (2013.01); *D04H 1/4291* (2013.01); *D04H 1/435* (2013.01); *D04H 1/4382* (2013.01); *D04H 1/4391* (2013.01); *D04H 1/46* (2013.01); *D04H 1/492* (2013.01)

(58) Field of Classification Search
CPC .......... A61F 2013/530167; A61F 2013/53016; A61F 2013/530452; A61F 2013/530459
See application file for complete search history.

(56) References Cited

U.S. PATENT DOCUMENTS 6,060,638 A * 5/2000 Paul ................. A61F 13/15203
604/367
2005/0136773 A1* 6/2005 Yahiaoui ............... A61F 13/537
442/394

(Continued)

FOREIGN PATENT DOCUMENTS

| EP | 1 504 739 A1 | 2/2005 |
| EP | 2 692 321 | 2/2014 |
| WO | WO 1997/023182 A1 | 7/1997 |

OTHER PUBLICATIONS

Translation of EP-2692321.*
International Search Report and Written Opinion for (PCT/US2015/034337) dated Sep. 15, 2015.

*Primary Examiner* — Bradley H Philips
(74) *Attorney, Agent, or Firm* — George H. Leal (57) ABSTRACT

A carded staple fiber nonwoven having a basis weight of between about 45 grams per square meter (gsm) and about 150 gsm, includes a blend of absorbing fibers, stiffening fibers and filler fibers. The carded staple fiber nonwoven is non-heat stiffened, has an air permeability of between about 100 m$^3$/m$^2$/min and about 500 m$^3$/m$^2$/min, and a pore radius mode of between about 60 μm and about 120 μm.

17 Claims, 6 Drawing Sheets

(51) Int. Cl.
*D04H 1/435* (2012.01)
*D04H 1/425* (2012.01)
*D04H 1/4291* (2012.01)
*A61F 13/537* (2006.01)
*D04H 1/4391* (2012.01)
*D04H 1/46* (2012.01)
*D04H 1/4382* (2012.01)
*D04H 1/492* (2012.01)

(56) References Cited

U.S. PATENT DOCUMENTS

| | | | |
|---|---|---|---|
| 2008/0113574 A1* | 5/2008 | Neron | A61F 13/0203 442/334 |
| 2008/0119806 A1* | 5/2008 | Nguyen | A61F 13/53 604/366 |
| 2012/0238978 A1 | 9/2012 | Weisman et al. | |

* cited by examiner

CARDED STAPLE FIBER NONWOVENS

TECHNICAL FIELD

The present disclosure generally relates to carded staple fiber nonwovens having improved performance characteristics, and disposable absorbent articles that contain the carded staple fiber nonwovens having improved performance characteristics.

BACKGROUND

Disposable absorbent articles such as feminine hygiene products, taped diapers, pant-type diapers and incontinence products are designed to absorb fluids from the wearer's body. Users of such disposable absorbent articles have several concerns. Leakage from products like catamenial pads, diapers, sanitary napkins, and incontinence pads is a significant concern. Comfort and the feel of the product against the wearer's body is also a concern. To provide better comfort, current disposable absorbent articles are typically provided with a topsheet that is flexible, soft feeling, and non-irritating to the wearer's skin. The topsheet does not itself hold the discharged fluid. Instead, the topsheet is fluid-permeable to allow the fluids to flow into an absorbent core.

Once the fluids flow into the absorbent core, the fluid may be held in the core by absorbent materials such as airfelt, particles of absorbent gelling material (AGM), and/or foaming absorbent material (FAM). In absorbent articles that include AGM, it may be important to contain the particles of AGM within the core so that the particles do not migrate to other parts of the absorbent article and/or outside of the absorbent article. It may also be important to maintain user comfort during and/or after the absorbent core has swelled from absorption of an amount of fluid.

To help ensure that fluids flow into the absorbent core, some disposable absorbent articles are further constructed with what is sometimes referred to as a secondary topsheet (STS) directly beneath the topsheet. This secondary topsheet is designed to acquire the fluid from a liquid-permeable topsheet and distribute it to the underlying absorbent core. Improving the ability of the STS to acquire and distribute liquid will address the user concerns of leakage and body feel, and can improve dryness of the topsheet by dewatering the topsheet. Improving additional characteristics of the STS may address further concerns such as AGM particle migration from the core and user comfort during and/or after the absorbent core has absorbed an amount of fluid. Accordingly, the development of new and improved secondary topsheet materials is of continued interest.

SUMMARY

In accordance with one embodiment, a carded staple fiber nonwoven has a basis weight of between about 45 grams per square meter (gsm) and about 150 gsm and is manufactured from a blend of absorbing fibers, stiffening fibers and filler fibers, wherein the carded staple fiber nonwoven is non-heat stiffened, has an air permeability of between about 100 $m^3/m^2$/min and about 500 $m^3/m^2$/min, and a pore volume radius mode of between about 60 μm and about 120 μm.

In accordance with another embodiment, a carded staple fiber nonwoven includes about 10% to about 50%, by weight, of stiffening fibers comprising hollow, spiral fibers formed from polyethylene terephthalate (PET), wherein the fibers have a linear density of between about 6 dtex and about 15 dtex; about 10% to about 50%, by weight, of absorbing fibers comprising tri-lobal fibers formed from rayon, wherein the fibers have a linear density of between about 2 dtex and about 6 dtex; and about 1% to about 60%, by weight, of filler fibers comprising solid, round fibers formed from polypropylene (PP), wherein the fibers have a linear density of about 3 dtex or greater, wherein the carded staple fiber nonwoven has a basis weight of between about 40 grams per square meter (gsm) and about 150 gsm, is non-heat stiffened, has an air permeability of between about 100 $m^3/m^2$/min and about 500 $m^3/m^2$/min, and a pore volume radius mode of between about 60 μm and about 120 μm.

In an additional form, a carded staple fiber nonwoven includes about 15% to about 35%, by weight, of stiffening fibers comprising hollow, spiral fibers formed from polyethylene terephthalate (PET), wherein the fibers have a linear density of between about 6 dtex and about 15 dtex; about 10% to about 50%, by weight, of absorbing fibers comprising tri-lobal fibers formed from rayon, wherein the fibers have a linear density of between about 2 dtex and about 6 dtex; and about 1% to about 60%, by weight, of filler fibers comprising solid, round fibers formed from polypropylene (PP), wherein the fibers have a linear density of about 3 dtex or greater, wherein the carded staple fiber nonwoven has a basis weight of between about 40 grams per square meter (gsm) and about 150 gsm, is non-heat stiffened, has an air permeability of between about 100 $m^3/m^2$/min and about 500 $m^3/m^2$/min, and a pore volume radius mode of between about 60 μm and about 120 μm.

While the specification concludes with claims particularly pointing out and distinctly claiming the subject matter that is regarded as the present invention, it is believed that the invention will be more fully understood from the following description taken in conjunction with the accompanying drawings. Some of the figures may have been simplified by the omission of selected elements for the purpose of more clearly showing other elements. Such omissions of elements in some figures are not necessarily indicative of the presence or absence of particular elements in any of the exemplary embodiments, except as may be explicitly delineated in the corresponding written description. None of the drawings are necessarily to scale.

DETAILED DESCRIPTION

As used herein, the following terms shall have the meaning specified thereafter:

"Absorbent article" refers to wearable devices, which absorb and/or contain liquid, and more specifically, refers to devices, which are placed against or in proximity to the body of the wearer to absorb and contain the various exudates discharged from the body. Absorbent articles can include diapers, training pants, adult incontinence undergarments (e.g., liners, pads and briefs) and/or feminine hygiene products.

The "longitudinal" direction is a direction running parallel to the maximum linear dimension, typically the longitudinal axis, of the article and includes directions within 45° of the longitudinal direction. "Length" of the article or component thereof, when used herein, generally refers to the size/distance of the maximum linear dimension, or typically to the size/distance of the longitudinal axis, of an article or part thereof.

The "lateral" or "transverse" direction is orthogonal to the longitudinal direction, i.e. in the same plane of the majority of the article and the longitudinal axis, and the transverse direction is parallel to the transverse axis. "Width" of the article or of a component thereof, when used herein, refers to the size/distance of the dimension orthogonal to the longitudinal direction of the article or component thereof, i.e. orthogonal to the length of the article or component thereof, and typically it refers to the distance/size of the dimension parallel of the transverse axis of the article or component.

The "Z-direction" is orthogonal to both the longitudinal and transverse directions.

"Machine Direction" or "MD" as used herein means the direction parallel to the flow of the carded staple fiber nonwoven through the nonwoven making machine and/or absorbent article product manufacturing equipment.

"Cross Machine Direction" or "CD" as used herein means the direction parallel to the width of the carded staple fiber nonwoven making machine and/or absorbent article product manufacturing equipment and perpendicular to the machine direction.

"Absorbent core" refers to a structure typically disposed between a topsheet and backsheet of an absorbent article for absorbing and containing liquid received by the absorbent article. The absorbent core may comprise one or more substrate layer(s), absorbent material disposed on the one or more substrate layer(s), and a thermoplastic adhesive composition on the absorbent material. The thermoplastic adhesive composition may be on the absorbent material and at least a portion of the one or more substrate layer. In a certain embodiment, the absorbent core would consist essentially of the one or more substrate layers, the absorbent material, the thermoplastic adhesive composition, and optionally a cover layer.

"Nonwoven material" refers to a manufactured web of directionally or randomly orientated fibers, excluding paper and products which are woven, knitted, tufted, stitch-bonded incorporating binding yarns or filaments, or felted by wet-milling, whether or not additionally needled. Nonwoven materials and processes for making them are known in the art. Generally, processes for making nonwoven materials comprise laying fibers onto a forming surface, which can comprise spunlaying, meltblowing, carding, airlaying, wet-laying, coform and combinations thereof. The fibers can be of natural or man-made origin and may be staple fibers or continuous filaments or be formed in situ.

The term "hydrophilic" describes fibers or surfaces of fibers, which are wettable by aqueous fluids (e.g., aqueous body fluids) deposited on these fibers. Hydrophilicity and wettability are typically defined in terms of contact angle and the strike-through time of the fluids, for example through a nonwoven fabric. This is discussed in detail in the American Chemical Society publication entitled "Contact Angle, Wettability and Adhesion", edited by Robert F. Gould (Copyright 1964). A fiber or surface of a fiber is said to be wetted by a fluid (i.e., hydrophilic) when either the contact angle between the fluid and the fiber, or its surface, is less than 90°, or when the fluid tends to spread spontaneously across the surface of the fiber, both conditions are normally co-existing. Conversely, a fiber or surface of the fiber is considered to be "hydrophobic" if the contact angle is greater than 90° and the fluid does not spread spontaneously across the surface of the fiber.

The term "Pore Volume Ratio" means the ratio of the peak of the pore volume versus the pore radii curve divided by the width of the same pore radii curve at half the peak of the pore volume.

The term "Pore Volume Radius Mode" means the radius at which the peak of the pore volume versus pore radii curve occurs.

The term "Pore Volume Factor" is the product of the Pore Volume Ratio and the Pore Volume Radius Mode.

A carded staple fiber nonwoven as disclosed herein can be used in a variety of disposable absorbent articles, but is particularly useful in diapers, feminine hygiene products and incontinence products such as sanitary napkins and incontinence pads. One non-limiting embodiment of a disposable absorbent article that incorporates a carded staple fiber nonwoven as detailed herein is shown as a sanitary napkin in FIGS. 1 and 2. In another embodiment, an incontinence pad incorporates a carded staple fiber nonwoven as detailed herein. Although a sanitary napkin will be specifically illustrated and described within this application, any of the features or elements of the sanitary napkin that are disclosed are also contemplated for any other embodiment of absorbent article, including incontinence pads.

Figure 1:
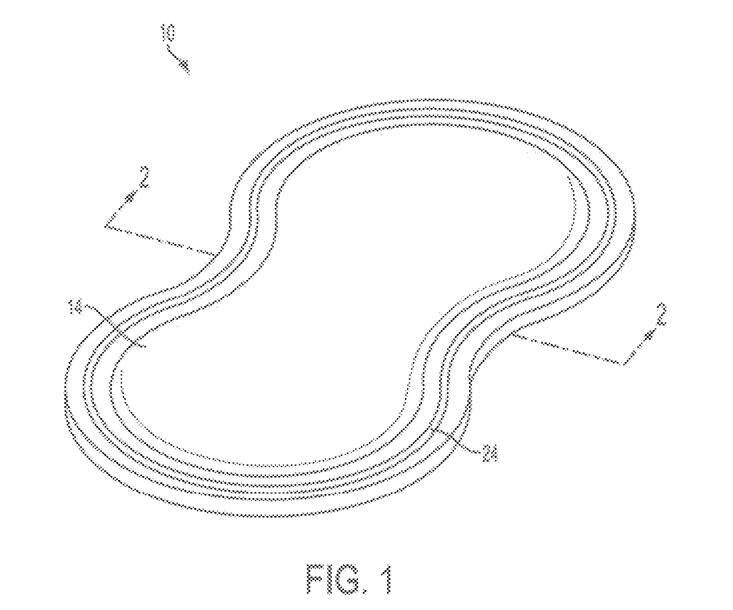
FIG. 1 is a perspective view of one example of a sanitary napkin that incorporates a carded staple fiber nonwoven.

A sanitary napkin 10 can have any shape known in the art for feminine hygiene articles, including the generally symmetric "hourglass" shape as shown in FIG. 1, as well as pear shapes, ovals, oblong ovals, pill shapes, bicycle-seat shapes, trapezoidal shapes, or wedge shapes. Sanitary napkins and pantiliners can also be provided with lateral extensions known in the art as "flaps" or "wings" (not shown in FIG. 1). Such extensions can serve a number of purposes, including, but not limited to, protecting the wearer's panties from soiling and keeping the sanitary napkin secured in place. The illustrated absorbent article has a body-facing upper side that contacts the user's body during use. The opposite, garment-facing lower side contacts the user's clothing during use.

The upper side of the sanitary napkin 10 generally has a topsheet 14 that can be liquid pervious. The lower side (seen in FIG. 2) has a backsheet 16 that can generally be liquid impervious and is joined with the topsheet 14 at the edges 12 of the sanitary napkin 10. In some embodiments of adult incontinence products not pictured herein, the topsheet and the backsheet are not joined at the edges. An absorbent core 18 is positioned between the topsheet 14 and the backsheet 16.

A secondary topsheet 20 can be provided at the top of the absorbent core 18, beneath the topsheet 14. As described in more detail below, the secondary topsheet 20 can be made of a carded staple fiber nonwoven as detailed herein. The topsheet 14, the backsheet 16, and the absorbent core 18 can be assembled in a variety of well-known configurations, including so called "tube" products or side flap products. Exemplary sanitary napkin configurations are described generally in U.S. Pat. No. 4,950,264, "Thin, Flexible Sanitary napkin"

issued to Osborn on Aug. 21, 1990, U.S. Pat. No. 4,425,130, "Compound Sanitary napkin" issued to DesMarais on Jan. 10, 1984; U.S. Pat. No. 4,321,924, "Bordered Disposable Absorbent Article" issued to Ahr on Mar. 30, 1982; U.S. Pat. No. 4,589,876; and "Shaped Sanitary napkin With Flaps" issued to Van Tilburg on Aug. 18, 1987.

The secondary topsheet 20 may take on any suitable shape. For example, the secondary topsheet 20 may follow the contours of the sanitary napkin shape, e.g. hourglass, pear shapes, ovals, oblong ovals, pill shapes, bicycle-seat shapes, trapezoidal shapes, or wedge shapes. In other forms, the secondary topsheet 20 may comprise a rectangular shape regardless of the shape of the sanitary napkin 10. In some forms, the secondary topsheet 20 may be longer in length than the absorbent core 18 or shorter than the absorbent core 18. In other forms, the secondary topsheet 20 may be positioned in a specific location, e.g. adjacent a lateral centerline of the sanitary napkin 10.

Figure 2:
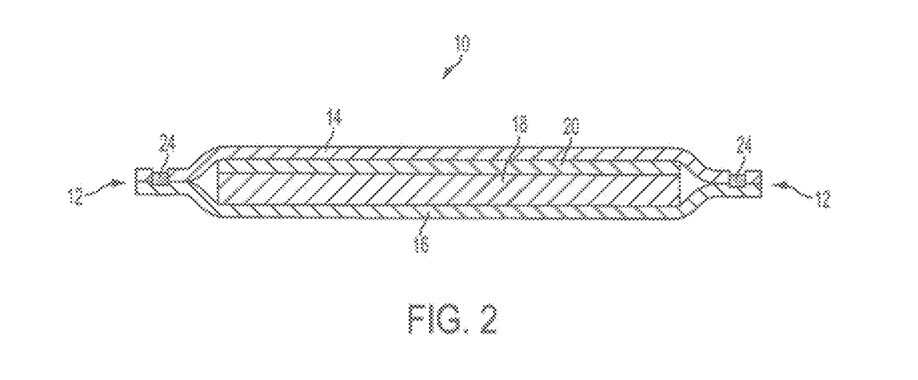
FIG. 2 is a cross-sectional view of the sanitary napkin of FIG. 1, taken through line 2-2.

The backsheet 16 and the topsheet 14, as shown in FIGS. 1 and 2, can be secured together in a variety of ways. Adhesives manufactured by H. B. Fuller Company of St. Paul, Minn. under the designation HL-1258 or H-2031 have been found to be satisfactory. Alternatively, the topsheet 14 and the backsheet 16 can be joined to each other by heat bonding, pressure bonding, ultrasonic bonding, dynamic mechanical bonding, a crimp seal, or by any other suitable securing method. As shown in FIG. 2, a fluid impermeable crimp seal 24 can resist lateral migration ("wicking") of fluid through the edges of the product, inhibiting side soiling of the wearer's undergarments.

As is typical for sanitary napkins and the like, the sanitary napkin 10 of the present disclosure can have panty-fastening adhesive disposed on the garment-facing side of backsheet 16. The panty-fastening adhesive can be any of known adhesives used in the art for this purpose, and can be covered prior to use by a release paper, as is well known in the art. If flaps or wings are present, a panty fastening adhesive can be applied to the garment facing side so as to contact and adhere to the underside of the wearer's panties.

To provide for softness next to the body, the topsheet 14 of the illustrated sanitary napkin 10 can be formed from a soft, smooth, flexible, porous material that is non-irritating to the user's skin. The topsheet 14 is permeable to the body fluids to be collected by the article and thus, for a sanitary napkin, is permeable to urine and other vaginal discharges. Generally, topsheets for absorbent articles can be made from a wide range of materials such as woven and nonwoven materials; polymeric materials such as apertured formed thermoplastic films, apertured plastic films, and hydro-formed thermoplastic films; porous foams; reticulated foams; reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers) or from a combination of natural and synthetic fibers.

Hydrophobic topsheets have a reduced tendency to allow fluids to pass back through and rewet the wearer's skin. Thus, the surface of the formed film (or nonwoven) that is in contact with the body remains dry, thereby reducing body soiling and creating a more comfortable feel for the wearer.

Example topsheets are hydrophobic topsheets selected from typical nonwoven forming approaches such as spun-bonded, carded, hydroentangled, needled, through-air bonded, or high loft nonwoven topsheets, and apertured 2-dimensional or 3-dimensional film topsheets. Lofty apertured formed film topsheets, with appreciable topsheet texture (nubs, micro-texture or with filament-like protrusions on the body-facing surface that can trap bodily discharges and hinder low fluid flows towards the body) that may be hydrophobic or hydrophilic in nature, can also be used. Apertured formed films are especially preferred for the topsheet 14 because they are pervious to body exudates and non-absorbent. However, for incontinence products, top-sheet materials other than formed films may be preferred. Some non-limiting examples are fibrous webs treated by mechanical formation to have increased softness or bulk properties, with or without a lotion applied thereto, as detailed in U.S. Pat. Nos. 7,732,657 and 7,553,532 to Hammons et al.

Still referring to FIG. 1, the absorbent core 18 of a sanitary napkin serves to store bodily fluids discharged during use. The absorbent core 18 can be manufactured in a wide variety of sizes and shapes, and may be profiled to have different thickness, hydrophilic gradients, superabsorbent gradients, densities, or average basis weights at different positions across the face of the sanitary napkin 10.

The absorbent core 18 can have a fluid distribution layer as well as a fluid storage layer, or in some embodiments, multiple distribution layers and/or multiple fluid storage layers, or any combination thereof. The fluid distribution layer may transfer the received fluid both downwardly and laterally, and generally has more permeability than the fluid storage layer. The carded staple fiber nonwovens detailed herein may also assist in transferring the received fluid both downwardly and laterally to the core. In addition to conventional absorbent materials such as creped cellulose wadding, fluffed cellulose fibers, Rayon fibers, wood pulp fibers also known as airfelt, and textile fibers, the fluid storage layer often includes superabsorbent material that imbibes fluids and form hydrogels. Such materials are also known as absorbent gelling materials (AGM), and may be included in particle form. AGM is typically capable of absorbing large quantities of body fluids and retaining them under moderate pressures. Synthetic fibers including cellulose acetate, polyvinyl fluoride, polyvinylidene chloride, acrylics (such as ORLON), polyvinyl acetate, non-soluble polyvinyl alcohol, polyethylene, polypropylene, polyamides (such as nylon), polyesters, bicomponent fibers, tricomponent fibers, mixtures thereof and the like can also be used in the fluid storage layer. The fluid storage layer can also include filler materials, such as PERLITE, diatomaceous earth, VERMICULITE, or other suitable materials, that lower rewet problems.

In some embodiments, portions of the fluid storage layer of the absorbent core 18 can be formed only of superabsorbent material, or can be formed of superabsorbent materials dispersed in a suitable carrier such as cellulose fibers in the form of fluff or stiffened fibers. One example of a non-limiting absorbent core 18 is a first layer formed only of superabsorbent material that is disposed on a second layer that is formed from a dispersion of superabsorbent material within cellulose fibers.

Figure 3:
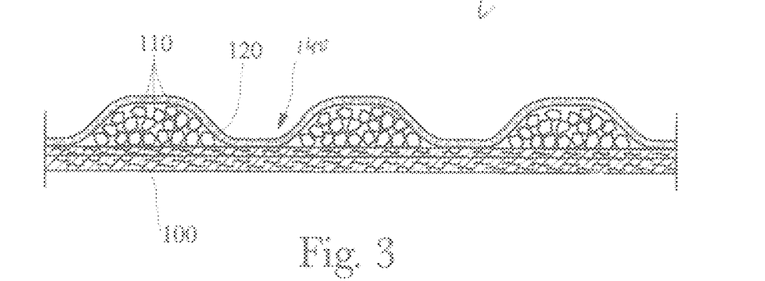
FIG. 3 is a cross-sectional view of an embodiment of an absorbent core of the sanitary napkin of FIG. 1, taken through line 2-2.
Figure 4:
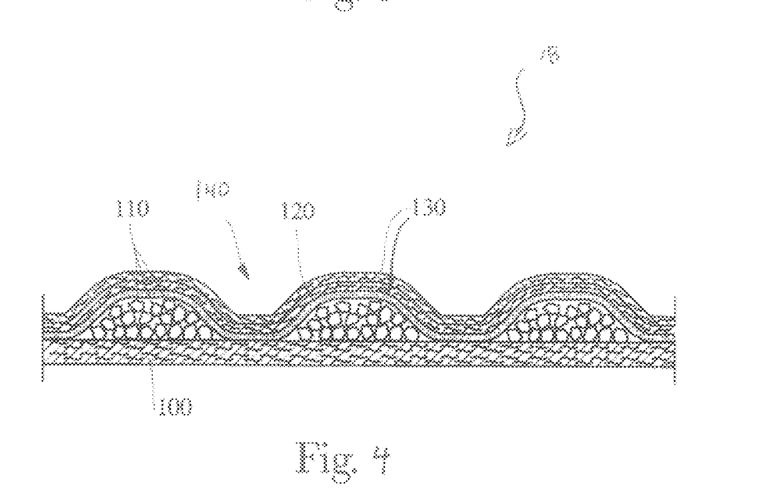
FIG. 4 is a cross-sectional view of an alternate embodiment of an absorbent core of the sanitary napkin of FIG. 1, taken through line 2-2.
Figure 5:
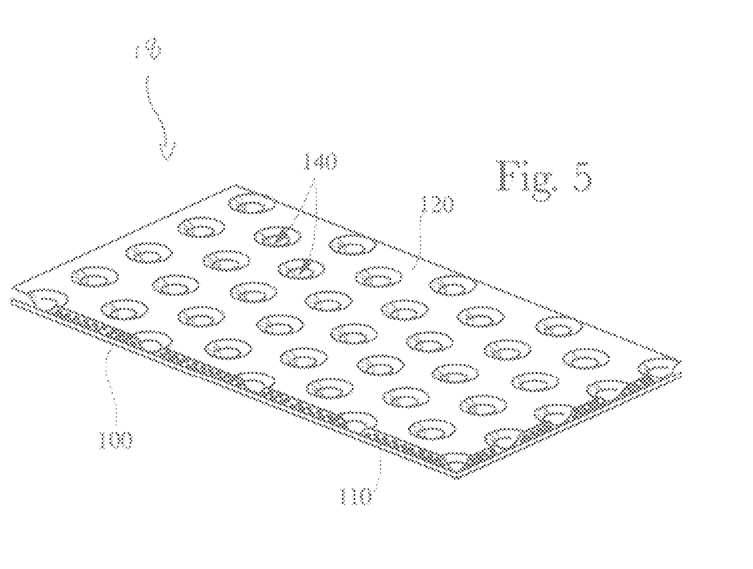
FIG. 5 is a perspective view of the embodiment of the absorbent core of FIG. 3.
Figure 6:
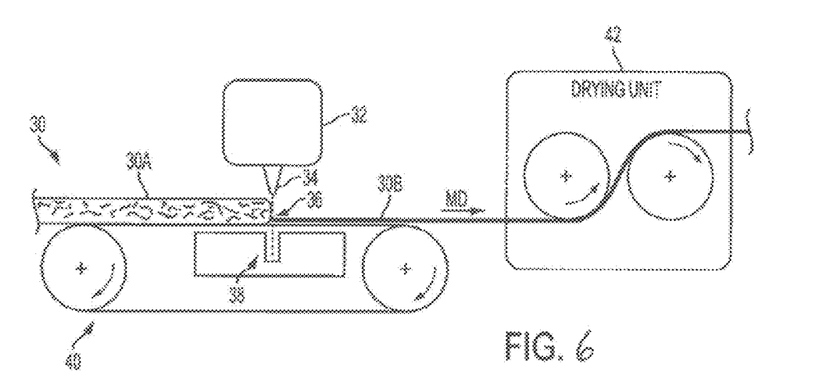
FIG. 6 depicts a simplified, schematic view of one example of a continuous carded staple fiber nonwoven manufacturing process.

Detailed examples of absorbent cores formed of layers of superabsorbent material and/or layers of superabsorbent material dispersed within cellulose fibers that may be utilized in the absorbent articles (e.g., sanitary napkins, incontinence products) detailed herein are disclosed in U.S. Patent Publication No. 2010/0228209 A1. As illustrated in FIGS. 3-5 herein, absorbent core 18 can comprise a substrate layer 100, a layer of absorbent polymer material (e.g., AGM) 110, and a layer of adhesive 120. Typically the adhesive can be a hot melt adhesive. In an embodiment of the present invention, the layer of adhesive 120 is a layer of fiberized hot melt adhesive. The areas where the hot melt adhesive 120 is in direct contact with the substrate layer 100 are the areas of junction 140. The substrate layer 100 can, for example, comprise a fibrous material, or can comprise a dispersion of superabsorbent material within cellulose fibers. An alternative embodiment of absorbent core 18 is shown in FIG. 4. The absorbent core 18 shown in FIG. 4 can further comprise one or more cover layer(s) 130. Non-limiting suitable materials for the cover layer(s) can include nonwoven materials.

The substrate layer 100 comprises a first surface and a second surface. Conventionally, in all the sectional views illustrated in the attached drawings the first surface of each layer is meant to correspond to the top surface, in turn, unless stated otherwise, corresponding to the wearer facing surface of the sanitary napkin 10 incorporating the absorbent core, while the second surface corresponds to the bottom surface, hence in turn the garment facing surface. At least portions of the first surface of the substrate layer 100 are in contact with a layer of absorbent polymer material 110. This layer of absorbent polymer material 110 comprises a first surface and a second surface, and can be typically a uniform or non-uniform layer, wherein by "uniform" or "non-uniform" it is meant that the absorbent polymer material 110 can be distributed over the substrate layer 100 respectively with uniform or non-uniform basis weight over the area interested by the distribution. Conversely, the second surface of the layer of absorbent polymer material 110 is in at least partial contact with the first surface of the substrate layer 100. According to an embodiment of the absorbent core 18, the layer of absorbent polymer material 110 can also be a discontinuous layer that is a layer typically comprising openings 140, i.e., areas substantially free of absorbent polymer material, which in certain embodiments can be typically completely surrounded by areas comprising absorbent polymer material. Typically these openings 140 have a diameter or largest span of less than 10 mm, or less than 5 mm, or 3 mm, or 2 mm, or 1.5 mm and of more than 0.5 mm, or 1 mm.

At least portions of the second surface of the absorbent polymer material layer 110 are in contact with at least portions of the first surface of the substrate layer material 100. The first surface of the layer of absorbent polymer material 110 defines a certain height of the layer of absorbent polymer material above the first surface of the layer of substrate material 100. When the absorbent polymer material layer 110 is provided as a non-uniform layer, typically for example as a discontinuous layer, at least some portions of the first surface of the substrate layer 100 are not covered by absorbent polymer material 110. The absorbent core 18 further comprises a layer of adhesive 120, for example typically a hot melt adhesive. This hot melt adhesive 120 serves to at least partially immobilize the absorbent polymer material 110. According to an embodiment of the present invention, the adhesive 120 can be typically a fiberized hot melt adhesive, i.e., being provided in fibres as a fibrous layer.

In an alternative embodiment of the present invention, as illustrated in FIG. 4, the absorbent core 18 can further comprise one or more cover layer(s) 130 having respective first and second surface, positioned such that the second surface of the cover layer 130 is in contact with the first surface of the layer of typically hot melt adhesive 120. However, embodiments of the absorbent core 18 of sanitary napkin 10 detailed herein may not need a cover layer 130 because the function of the cover layer (i.e., containing superabsorbent material within the absorbent core) is now being performed by the secondary topsheet 20, as later detailed herein. In some embodiments, the absorbent core 18 may include a cover layer 130, and the absorbent article (e.g., sanitary napkin 20) that contains the absorbent core 18 may also include a secondary topsheet 20 as detailed herein.

Further details of suitable absorbent cores 18 for the absorbent articles detailed herein may be found in the disclosure of U.S. Patent Publication No. 2010/0228209 A1. However structured, the total absorbent capacity of the absorbent core 18 should be compatible with the design loading and the intended use of the article (e.g., sanitary napkin 10 or an incontinence pad). Thus, the size and absorbent capacity of the absorbent core 18 can be varied to accommodate different uses such as larger incontinence pads, incontinence briefs, pantiliners, regular sanitary napkins, or overnight sanitary napkins.

The absorbent articles detailed herein may also have integrated or attached cuffs (e.g., incontinence articles with barrier leg cuffs attached to the longitudinal edges of the article). The leg cuffs may take the form of absorbent article leg cuffs known in the art. In one non-limiting example, the article can have leg cuffs as described in U.S. Patent Publication No. 2011/0319855 A1.

Referring again to FIG. 1, the backsheet 16 that covers the lower side of the absorbent core 18 prevents the fluids in the absorbent core 18 from wetting articles that contact the sanitary napkin 10, such as pants, pajamas and undergarments. Accordingly, the backsheet 16 is preferably made from a liquid impervious thin film or a liquid impervious but vapor pervious film/nonwoven laminate, a microporous film, an apertured formed film, or other polymer film that is vapor permeable, or rendered to be vapor permeable, but substantially impervious to fluid.

The secondary topsheet 20 is interposed between the absorbent core 18 and the topsheet 14, and serves to rapidly draw discharged body fluids, in particular menstrual fluids and/or urine, through the adjacent permeable (primary) topsheet 14. This allows the surface of the primary topsheet 14 adjacent the wearer of the article to remain relatively clean and dry (it also provides acquisition/distribution functions). The secondary topsheet 20 in the illustrated sanitary napkin 10 has a carded, hydroentangled (e.g., spunlaced) staple fibrous web or matrix that is comprised of a plurality of fiber types.

Generally, the secondary topsheet 20 manufactured with a carded staple fiber nonwoven in accordance with the present disclosure provides capillary suction to "pull" fluid through the topsheet 14, which is competing for trickle/low flow conditions. The secondary topsheet 20 also can contain a gush by providing distribution functions to efficiently utilize the absorbent core 18, as well as provide intermediate storage until the absorbent core 18 can accept fluid. In addition, the secondary topsheet 20 can have a pore size in which a majority of the pores are sized smaller than the AGM particles used in the absorbent core 18 (AGM particles are typically greater than about 200 microns—i.e., the particles will not fit through a 200 micron sieve). Thus, the pore size of the secondary topsheet restricts the AGM particles from passing through the secondary topsheet. Accordingly, the pore size of the secondary topsheet 20 can be both large enough to enable quick fluid acquisition and distribution into the absorbent core 18, but small enough so that very little, if any, AGM particles of the absorbent core are able to pass through the secondary topsheet. Further, if the pore size distribution of the secondary topsheet 20 is narrow, it is also possible to have a larger average pore size while still having a low number of pores that are larger than the AGM particles. Pore size distribution can be expressed in a pore volume ratio parameter and/or the pore volume factor, which is measured as detailed below in the methods section. In some embodiments of the articles detailed herein, the pore volume ratio can be greater than about 6, or greater than about 8, or greater than about 10. The pore volume factor can be greater than about 500 mm$^3$/µm·g. In some forms, the pore volume factor may be greater than about 600 mm$^3$/µm·g or greater than about 700 mm$^3$/µm·g or greater than about 800 mm$^3$/µm·g or about 900 mm$^3$/µm·g. In some forms, the pore volume factor may be between about 500 mm$^3$/µm·g to about 900 mm$^3$/µm·g or from about 600 mm$^3$/µm·g to about 800 mm$^3$/µm·g specifically including all values within these ranges and any ranges created thereby. Pore size distribution can also be expressed in a pore volume radius mode, which is measured as detailed in the methods herein. In some embodiments of the articles detailed herein, the pore volume radius mode can be between about 60 µm and about 120 µm, or between about 65 µm and about 105 µm, or between about 70 µm and about 90 µm.

Sometimes an absorbent core 18 that includes AGM further includes a cover layer (shown in FIG. 4) to ensure that AGM does not migrate from the absorbent core. However, if the secondary topsheet 20 has a pore structure that does not allow AGM to pass through, the cover layer 130 may be eliminated from the absorbent core 18 construction, saving on costs and environmental impact of the disposable absorbent articles. Also, with less layers (e.g., minus cover layer), the article will have better fluid handling by reducing the layers that the fluid needs to pass through, therefore moving fluid quicker to core and away from the topsheet, thus improving dryness.

The secondary topsheet 20 can also provide stiffness and flexural rigidity in addition to or in combination with the core which is generally required to prevent, or at least attempt to reduce, cross machine direction (CD) bunching while maintaining comfort and body fit. Accordingly, the secondary topsheet 20 may possess sufficient strength to withstand the swelling of the AGM in the core and the mechanical stresses of user wear, therefore reducing and/or preventing bunching of the absorbent article and providing additional comfort to the user. The secondary topsheet 20 may also be compression resistant and resilient (both dry and wet) to maintain the permeability and capacity of the secondary topsheet and improve acquisition and dryness for the absorbent article while in use.

The carded staple fiber nonwoven of the secondary topsheet 20 can have a basis weight of 175 grams per square meter (gsm) or less; or a basis weight of 150 gsm or less; or a basis weight in the range of about 30 gsm to about 150 gsm; or in the range of about 45 gsm to about 150 gsm; or in the range of about 45 gsm to about 85 gsm; or in the range of about 55 gsm to about 100 gsm, or in a range of about 50 gsm to about 75 gsm including any values within these ranges and any ranges created thereby. The carded staple fiber nonwoven of the secondary topsheet 20 can also have a cross machine direction (CD) flexural rigidity of about 0.01 mN·cm to about 10 mN·cm. In some embodiments, the carded staple fiber nonwoven has a CD flexural rigidity of about 0.05 mN·cm to about 2 mN·cm or from about 0.07 mN·cm to about 1.0 mN·cm or from about 0.08 mN·cm to about 0.3 mN·cm including any values within these ranges and any ranges created thereby. In some embodiments, the carded staple fiber nonwoven has a MD flexural rigidity of less than about 4.8 mN·cm. In some embodiments, the MD flexural rigidity can be greater than about 0.59 mN·cm. The MD flexural rigidity can be from about 0.60 mN·cm to about 3 mN·cm specifically including all values within this range and all ranges created thereby.

As noted previously, it may be desirable to have stiffness and flexural rigidity in the CD to reduce bunching while maintaining comfort and body fit. For this reason, in some forms, it may be beneficial for the flexural rigidity in the CD to be close to the flexural rigidity of the MD. In some embodiments, the CD flexural rigidity/MD flexural rigidity can be between about 5% to about 32.4% or from about 5.2% to about 7.3%, specifically including all values within these ranges and all ranges created thereby.

The carded staple fiber nonwoven of the secondary topsheet 20 can also have a caliper of greater than about 0.09 and less than about 0.20 mm per 10 gsm. In some embodiments, the carded staple fiber nonwoven of the secondary topsheet 20 can also have caliper of about 0.9 mm to about 1.2 mm for a basis weight of about 55 gsm to about 75 gsm. The carded staple fiber nonwoven of the secondary topsheet 20 can also have a density of about 0.05 g/cc to about 0.10 g/cc, or from about 0.06 g/cc to about 0.09 g/cc specifically including any values within these ranges and any ranges created thereby.

The carded staple fiber nonwoven of the secondary topsheet 20 can be manufactured from an assortment of suitable fiber types that produce the desired mechanical performance and fluid handling performance. In some embodiments, the carded staple fiber nonwoven may be formed from a combination of stiffening fibers, absorbing fibers and filler fibers. The stiffening fibers, for example, can form about 10% to about 50%, by weight, of the carded staple fiber nonwoven. For some example secondary topsheets, the stiffening fibers can form about 15% to 35%, by weight, of the carded staple fiber nonwoven. In other embodiments, the stiffening fibers can form about 25%, by weight, of the carded staple fiber nonwoven.

The stiffening fibers can be polyethylene terephthalate (PET) fibers, or other suitable non-cellulosic fibers known in the art. For carded staple fiber nonwovens including PET fibers, the PET fibers can have a dtex in the range of about 3.5 to about 15.0, or in the range of about 6.0 to about 12.0. The staple length of the stiffening fibers can be in the range of about 28 mm to about 100 mm, or in the range of about 37 mm to about 50 mm. Some carded staple fiber nonwovens include stiffening fibers with a staple length of about 38 mm to 42 mm. The PET fibers can have any suitable structure or shape. For example, the PET fibers can be round or have other shapes, such as spiral, scalloped oval, trilobal, scalloped ribbon, and so forth. Further, the PET fibers can be solid, hollow or multi-hollow. In some embodiments of the carded staple fiber nonwoven, the stiffening fibers may be fibers made of hollow/spiral PET. Optionally, the stiffening fibers may be spiral-crimped or flat-crimped. The stiffening fibers may have a crimp value of between about 4 and about 12 crimps per inch (cpi), or between about 4 and about 8 cpi, or between about 5 and about 7 cpi, or between about 9 and about 10 cpi. Particular non-limiting examples of stiffening fibers can be obtained from Wellman, Inc. Ireland under the trade names H1311 and T5974. Other examples of suitable stiffening fibers for utilization in the carded staple fiber nonwovens detailed herein are disclosed in U.S. Pat. No. 7,767,598 to Schneider et al.

In other embodiments, the stiffening fibers may be so-called bi-component fibers, where individual fibers are provided from different materials, usually a first and a second polymeric material. The two materials may be chemically different (hence the fibers are chemically heterogeneous) or they may differ only in their physical properties while being chemically identical (hence the fibers are chemically homogeneous). For example, may the intrinsic viscosity of the two materials be different, which has been found to influence the crimping behavior of the bi-component fibers. Bi-component fibers that are suitable as stiffening fibers are side-by-side bi-component fibers as disclosed for example in WO 99/00098.

Another suitable bi-component stiffening fiber is a fiber of circular cross section with a hollow space in the centre that is spiral crimped. It is preferred that 10-15% of the cross sectional area are hollow, more preferably 20-30% of the cross sectional area are hollow. Without wishing to be bound by theory, it is believed that the spiral crimping of fibers is beneficial for their liquid acquisition and distribution behaviour. It is assumed that the spiral crimp increases the void space in an acquisition member formed by such fibers. Often, an absorbent article, when being worn, is exposed to a certain pressure exerted by the wearer, which potentially decreases the void space in the acquisition member. Having good permeability and sufficient void space available are important for good liquid distribution and transport. It is further believed that the bi-component spiral-crimped fibers as described above are suitable to maintain sufficient void volume even when an acquisition member is exposed to pressure. Also, spiral-crimped fibers believed to provide for good permeability as for a given fiber dtex value, the hollow fiber cross-section allows for a larger outer diameter of the fiber as compared to a compact cross-section. The outer diameter of a fiber appears to determine the permeability behavior of an acquisition member formed by such fibers.

The absorbing fibers, for example, can form about 10% to about 50%, by weight, of the carded staple fiber nonwoven. For some example secondary topsheets, the absorbing fibers can form about 30% to about 40%, by weight, of the carded staple fiber nonwoven. In other embodiments, the absorbing fibers can form about 35%, by weight, of the carded staple fiber nonwoven.

The absorbing fibers can be rayon, such as viscose rayon, or other suitable cellulosic fibers known in the art, such as cotton (or a blend of these fibers). For carded staple fiber nonwovens including rayon, the rayon can have a dtex in the range of about 1.0 to about 8.0, or from about 2.0 to about 6.0. The staple length of the absorbing fibers can be in the range of about 20 mm to about 100 mm, or about 30 mm to about 50 mm or about 35 mm to about 45 mm. The rayon fibers can have any suitable structure or shape. For example, the rayon fibers can be round or have other shapes, such as spiral, scalloped oval, trilobal, other multi-lobal shapes, scalloped ribbon, and so forth. Further, the rayon fibers can be solid, hollow or multi-hollow. In some embodiments of the carded staple fiber nonwoven, the absorbing fibers may be trilobal in shape, or another shape with a multiple lobes in cross section. Other examples of suitable multi-lobed absorbing fibers for utilization in the carded staple fiber nonwovens detailed herein are disclosed in U.S. Pat. No. 6,333,108 to Wilkes et al, U.S. Pat. No. 5,634,914 to Wilkes et al., and U.S. Pat. No. 5,458,835 to Wilkes et al.

One advantage of multiple lobed absorbing fibers is their greater bulk over single-limbed fibers, because the circumferential area of the multiple lobed fibers is larger than their actual cross-sectional area. For example, Japanese Patent Application Kokai 61-113812 describes a filament yarn consisting of X- or Y-shaped continuous viscose filaments that is used in textile applications where bulk is important, for example in pile weaves. Another advantage of multi-limbed absorbing fibers is their increased absorbency over single-limbed fibers.

The filler fibers, for example, can form about 1% to about 80%, by weight, of the carded staple fiber nonwoven. For some example secondary topsheets, the filler fibers can form about less than about 60%, by weight, of the carded staple fiber nonwoven. In other embodiments, the filler fibers can form about 40%, by weight, of the carded staple fiber nonwoven.

The filler fibers can be any thermoplastic fiber, such as polypropylene (PP), or other suitable thermoplastic fibers known in the art. For carded staple fiber nonwovens including thermoplastic fibers, the fibers can have a dtex of greater than about 3.0. Some carded staple fiber nonwovens can include PP having a dtex in the range of about 4 to about 10. The staple length of the filler fibers can be in the range of about 20 mm to about 100 mm, or about 30 mm to about 50 mm or about 35 mm to about 45 mm. The thermoplastic fibers can have any suitable structure or shape. For example, the thermoplastic fibers can be round or have other shapes, such as spiral, scalloped oval, trilobal, scalloped ribbon, and so forth. Further, the PP fibers can be solid, hollow or multi-hollow. In some embodiments of the carded staple fiber nonwoven, the third filler fibers may be solid and round in shape. Other suitable examples of filler fibers include bi-component fibers such as polyethylene/polypropylene, polyethylene/polyethylene terephthalate, polypropylene/polyethylene terephthalate. These bi-component fibers may be configured as a sheath and a core.

The carded staple fiber nonwoven of the secondary topsheet 20 formed in accordance with the present disclosure imparts a number of desirable physical properties, including its narrow pore size distribution, wicking/capillarity, permeability, wet Z-direction crush resistance and flexural rigidity. Generally, the absorbing fibers of the carded staple fiber nonwoven, such as rayon, provide capillarity, which serves to transport fluid from the topsheet 14 to the absorbent core 18. The stiffening fibers of the carded staple fiber nonwoven, such as PET, provide Z-direction strength to prevent, or at least limit, collapse of the secondary topsheet 20 when wetted while also providing desirable permeability. The filler fibers of the carded staple fiber nonwoven, such as polypropylene fibers, serve to provide a cost effective way to increase basis weight of the material while having minimal effect on pore size distribution.

Methods of Making Carded Staple Fiber Nonwovens

FIG. 5 depicts a simplified, schematic view of one example of a continuous carded staple fiber nonwoven manufacturing process. As is to be appreciated, the carded staple fiber nonwoven produced by the process of FIG. 5 can be used in the manufacturing of a variety of absorbent articles, such as the sanitary napkin 10 of FIGS. 1-2, as well as a variety of other absorbent articles, including diapers, training pants, adult incontinence undergarments, and the like.

As is generally known in the art, hydroentanglement (sometimes referred to as spunlacing, jet entanglement, water entanglement, hydroentanglement or hydraulic needling), is a mechanical bonding process whereby fibers of a nonwoven web are entangled by means of high pressure water jets. Patterning can be achieved by use of patterned drums or belts which cause the fibers to form a negative image of the drum design in the fabric. The formed web of various fibrous components (usually airlaid, wetlaid, or carded, but sometimes spunbond or melt-blown, etc.) can first be compacted and prewetted to eliminate air pockets and then water-needled. With reference to FIG. 5, a fibrous structure 30 is formed from cellulosic fibers, non-cellulosic fibers and bicomponent fibers, e.g. filler fibers, absorbing fibers, and stiffening fibers. The fibrous structure 30 has an unbonded portion 30A upstream of a jet head 32 and a bonded (i.e., hydroentangled) portion 30B downstream of the jet head 32. During the entanglement process, the fibrous structure 30 is passed by the jet head 32 that comprises a plurality of injectors that are positioned to generally form a water curtain (for simplicity of illustration, only one injector 34 is illustrated in FIG. 5). A water jet 36 is directed through the fibrous structure 30 at high pressures, such as 150 or 400 bar. As is to be appreciated, while not illustrated, multiple rows of injectors 34 are typically used, which can be positioned on one or both sides of the fibrous structure 30.

The fibrous structure 30 can be supported by any suitable support system 40, such as a moving wire screen (as illustrated) or on a rotating porous drum, for example. While not illustrated, it is to be appreciated that hydroentanglement systems can expose the fibrous structure 30 to a series of jet heads 32 along the machine direction, with each delivering water jets at different pressures. The particular number of jet heads 32 utilized can be based on, for example, desired basis weight, degree of bonding required, characteristics of the web, and so forth. As the water jet 36 penetrates the web, a suction slot 38 positioned proximate beneath the fibrous structure 30 collects the water so that it can be filtered and returned to the jet head 32 for subsequent injection. The water jet 36 delivered by the jet head 32 exhausts most of its kinetic energy primarily in rearranging fibers within the fibrous structure 30 to turn and twist the fibers to form a series of interlocking knots.

Once the fibrous structure 30 has been hydroentangled (shown as bonded portion 30B), the fibrous structure 30 is then passed through a dewatering device where excess water is removed. In the process illustrated in FIG. 5, the dewatering device is a drying unit 42. The drying unit 42 can be any suitable drying system, such as a multi-segment multi-level bed dryer, a vacuum system, and/or an air drum dryer, for example. The drying unit 42, or other dewatering device, serves to substantially dry the fibrous structure 30. The term "substantially dry" is used herein to mean that the fibrous structure 30 has a liquid content, typically water or other solution content, less than about 10%, less than about 5%, or less than about 3%, by weight.

Once the fibrous structure 30 is manufactured in accordance with the present disclosure it can be incorporated into, for example, an absorbent material. With regard to the sanitary napkin 10 of FIGS. 1-2, the secondary topsheet 20 incorporating the fibrous structure 30 can be bonded to, or otherwise attached to the topsheet 14. In some embodiments, thermal point calendaring or other suitable bonding is utilized. In other embodiments, the fibrous structure 30 can serve as an absorbent core of an absorbent article. For example, pantiliners and incontinence pads can be formed with the fibrous structure 30 positioned between a topsheet and a bottom sheet to function as at least part of an absorbent core, as described above with respect to FIGS. 1-2. Furthermore, in some embodiments, the fibrous structure 30 does not include a binder component.

Presented below are data of the present invention compared to conventional samples of material. The data presented below was taken at two differing time points. The first set of data—provided in Table 1—was taken shortly after manufacture of the webs described herein. The second set of data—provided in Table 2—was taken after several months of the nonwoven webs being stored in roll form. Due to the storage, a reduction in caliper was noted as well as a reduction in permeability; however, the same trend in permeability was noted with regard to the nonwovens of the present invention versus the conventional nonwoven webs.

Test Methods

The following test methods were used.

(1). The measurements for fiber linear density provided herein were obtained by using the Standard Test Method for Linear Density of Textile Fibers, as detailed in ASTM Designation D1577-07.

(2). The measurements for fiber lengths provided herein were obtained by using the Standard Test Method for Length and Length Distribution of Manufactured Staple Fibers (Single-Fiber Test), as detailed in ASTM Designation D5103-07.

(3). The measurements for capacity provided herein were obtained by using Worldwide Strategic Partners (WSP) Test Method 10.1.

(4). The measurements for caliper provided herein were obtained by using Worldwide Strategic Partners (WSP) Test Method 120.6 using a 0.5 kpa load. For the later tested samples a 50.8 mm anvil diameter was used at 1.43 kPa load, 0.3 inches/second drop speed and 2 second dwell time.

(5). The measurements for MD bending length and CD bending length provided herein were obtained by using Worldwide Strategic Partners (WSP) Test Method 90.5. For the later tested samples, note that samples sizes were utilized which were 25 mm by at least 85 mm.

(6). The measurements for air permeability provided herein were obtained by using Worldwide Strategic Partners (WSP) Test Method 70.1. For the later tested samples a pressure drop of 125 Pa and an orifice 38.3 square centimeters was used.

(7). The measurements for basis weight provided herein were obtained by using Worldwide Strategic Partners (WSP) Test Method 130.1.

(8). The measurements for pore volume radius mode and pore volume ratio provided herein were obtained by the following method regarding pore volume distribution.

Pore Volume Distribution

Pore volume distribution measurements are made on a TRI/Autoporosimeter (TRI/Princeton Inc. of Princeton, N.J.) The TRI/Autoporosimeter is an automated computer-controlled instrument for measuring pore volume uptake and pore-size distribution in porous materials. Here, measurements are performed on an initially dry specimen using a 0.25 psi confining pressure during an absorption, desorption and second absorption cycle. Pores between 5 µm and 1000 µm are measured. Information on the TRI/Autoporosimeter, its operation and data treatments can be found in The Journal of Colloid and Interface Science 162(1994), pp. 163-170, incorporated here by reference.

Figure 7:
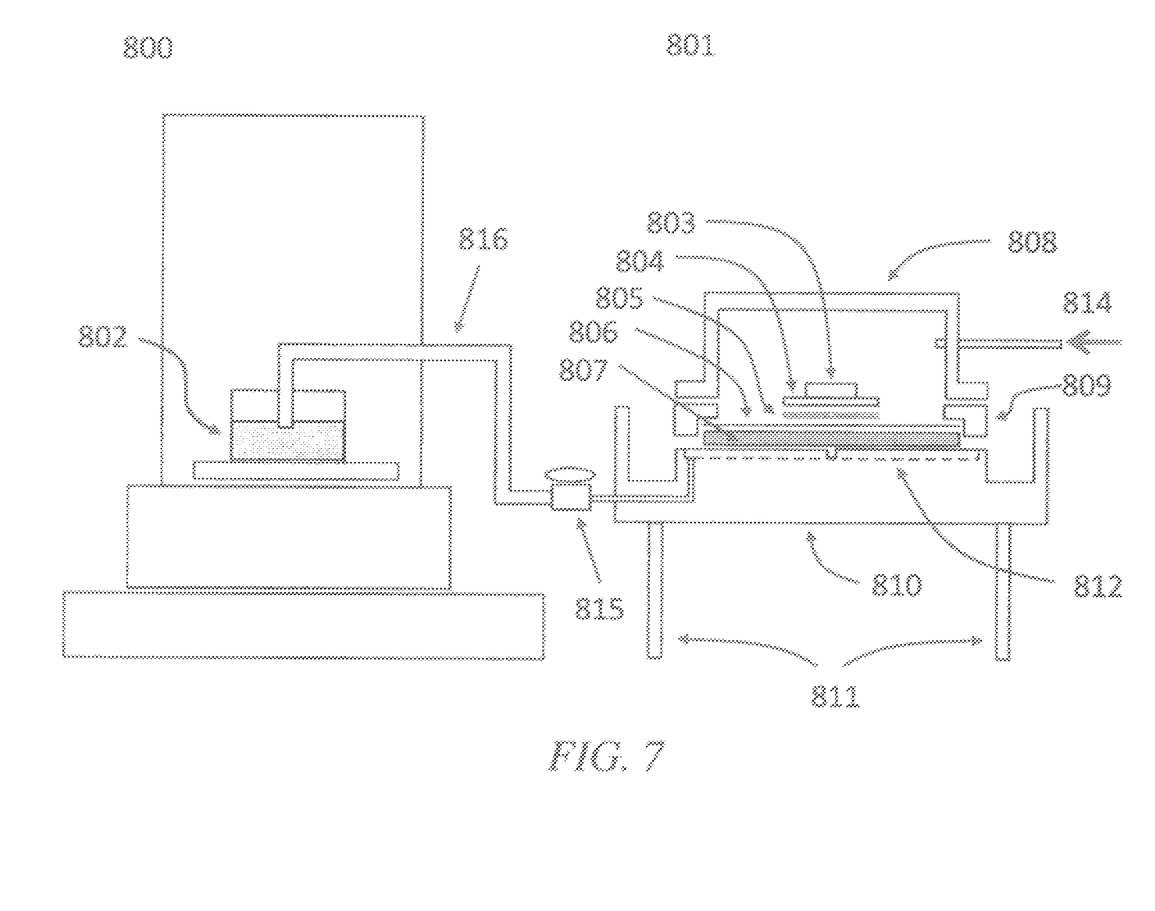
FIG. 7 depicts a schematic view of the equipment used to measure pore volume distribution.
Figure 8:
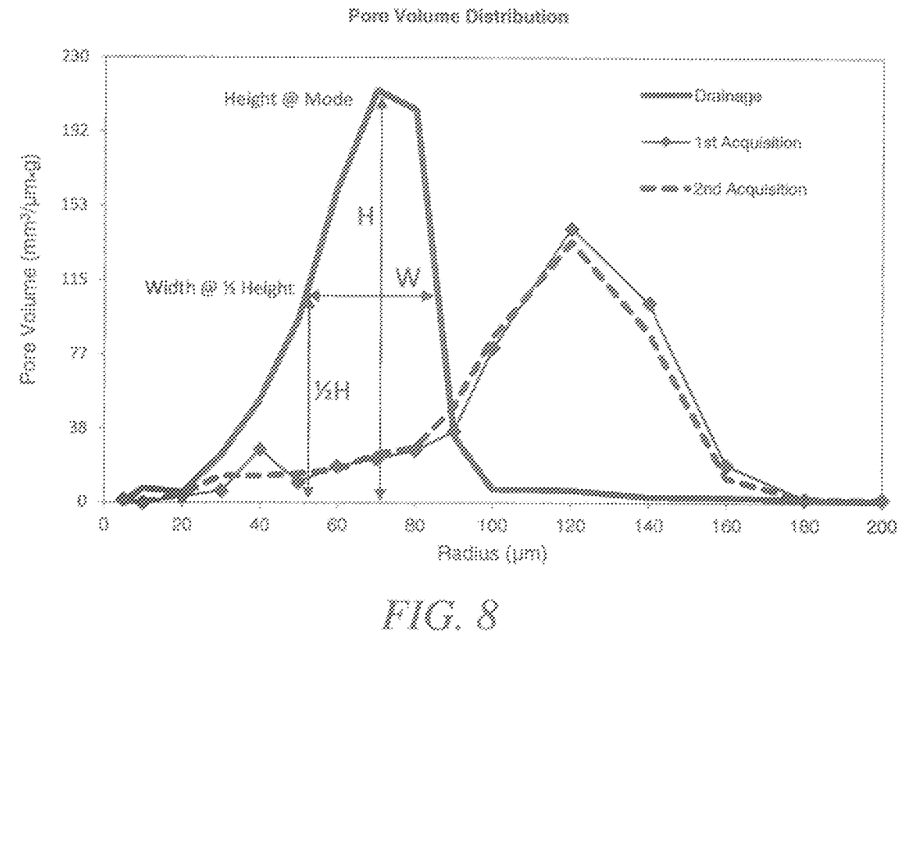
FIG. 8 depicts an example of a chart illustrating a pore volume distribution experiment cycle.

A representation of the TRI equipment is shown in FIG. 7 and consists of a balance 800 with fluid reservoir 801 which is in direct fluid communication with the sample 811 which resides in a sealed, air-pressurized sample chamber 810. An example experiment cycle is shown in FIG. 8.

Determining the Pore Volume Uptake or Pore-Size Distribution involves recording the increment of liquid that enters or leaves a porous material as the surrounding air pressure is altered. A sample in the test chamber is exposed to precisely controlled changes in air pressure. As the air pressure increases or decreases, the void spaces or pores of the porous media de-water or uptake fluid, respectively. Total fluid uptake is determined as the total volume of fluid absorbed by the porous media.

Pore-Size Distribution can further be determined as the distribution of the volume of uptake of each pore-size group, as measured by the instrument at the corresponding pressure. The pore size is taken as the effective radius of a pore and is related to the pressure differential by the following relationship.

$$\text{Pressure differential} = [2\gamma \cos \Theta]/\text{effective radius} \quad 5$$

where γ=liquid surface tension, and Θ=contact angle

For this experiment: γ=27 dyne/cm² divided by the acceleration of gravity; cos Θ=1°

The automated equipment operates by precisely changing the test chamber air pressure in user-specified increments, either by decreasing pressure (increasing pore size) to cause fluid uptake by the porous media, or by increasing pressure (decreasing pore size) to de-water the porous media. The liquid volume absorbed (drained) at each pressure increment yields the pore size distribution. The fluid uptake is the cumulative volume for all pores taken up by the porous media, as it progresses to saturation (e.g. all pores filled).

Experimental Conditions:

Take a 9 cm diameter, 0.22 μm membrane filter (mixed cellulose esters, Millipore GSWP, EMD Millipore Corp., Billerica Mass.) by adhering the filter to a 9 cm diameter by 0.6 cm thick Monel porous frit 807 using KRYLON® spray paint (FilmTools Gloss White Spray Paint #1501). Allow the frit/membrane to dry before use.

Fill the inner base 812 of the sample chamber with hexadecane (available from Sigma-Aldrich CAS #544-76-3). Place the frit 807 membrane side up onto the base of the sample chamber 810, and secure it into place with a locking collar 809. Fill the connecting tube 816, reservoir 802, and the fit 807 with hexadecane assuring that no bubbles are trapped within the connecting tube or the pores within the frit and membrane. Using the legs of the base 811, level the sample camber and align the membrane with the top surface of the fluid within the reservoir.

Dye cut a specimen 5.5 cm square. Measure the mass of the specimen to the nearest 0.1 mg. A 5.5 cm square, Plexiglas cover plate 804 and confining weight 803 are selected to provide a confining pressure of 0.25 psi.

Place the top of the sample chamber 808 in place and seal the chamber. Apply the appropriate air pressure to the cell (connection 814) to achieve a 5 μm effective pore radius. Close the liquid valve 815. Open the sample chamber, place the specimen 805, cover plate 804 and confining weight 803 into the chamber onto the membrane 806 and seal the camber. Open the liquid valve 815 to allow free movement of liquid to the balance.

Progress the system through a sequence of pore sizes (pressures) as follows (effective pore radius in μm): 5, 10, 20, 30, 40, 50, 60, 70, 80, 90, 100, 120, 140, 160, 180, 200, 250, 300, 350, 400, 450, 500, 550, 600, 700, 800, 1000, 800, 700, 600, 550, 500, 450, 400, 350, 300, 250, 200, 180, 160, 140, 120, 100, 90, 80, 70, 60, 50, 40, 30, 20, 10, 5, 10, 20, 30, 40, 50, 60, 70, 80, 90, 100, 120, 140, 160, 180, 200, 250, 300, 350, 400, 450, 500, 500, 550, 600, 700, 800, 1000. The sequence is progressed to the next radius when an equilibrium rate of less than 25 mg/min is measured at the balance.

In like fashion, measure the acquisition/drainage/acquisition cycle blank without a sample.

Based on the incremental volume values, calculate the blank-corrected values for cumulative volume versus equivalent pore radius.

Cumulative Volume (mm³/mg)=[Specimen Fluid Uptake (mg)−Blank Fluid Uptake (mg)]/Density of Hexadecane (g/cm³)/Sample Mass (mg)

Pore Volume (mm³/μm·g)=Change in Effective Radius (μm)/[Change in Cumulative Volume (mm³/mg)*1000]

Plot Pore Volume (mm³/μm·g) vs. Effective Radius (μm). Referring to FIG. 8, determine from the drainage curve, the Pore Volume value (H) at the mode of the Effective Radius. Where a vertical line parallel to the Y-axis extending from the value (H) to the X-axis defines Pore Volume Radius Mode. From the peak calculate the width (W) at half height (½ H) by connecting the data points with straight lines and calculate the Pore Volume Ratio as H/W and report to the nearest 0.01 mm³/μm·g/μm.

In Tables 1 and 2 below:

Sample 1 is a 55 gsm staple fiber nonwoven that was produced from a homogeneous blend of:
(a) 25% hollow, spiral polyethylene terephthalate fibers (10 dtex, staple length);
(b) 35% tri-lobal rayon fibers (3.3 dtex, staple length); and
(c) 40% round polypropylene fibers (6.7 dtex, staple length).

Sample 2 is a 75 gsm staple fiber nonwoven that was produced from a homogeneous blend of:
(a) 25% hollow, spiral polyethylene terephthalate fibers (10 dtex, staple length);
(b) 35% tri-lobal rayon fibers (3.3 dtex, staple length); and
(c) 40% round polypropylene fibers (6.7 dtex, staple length).

Sample 3 is a 55 gsm carded staple fiber nonwovens that was produced from a homogeneous blend of:
(a) 40% round viscose rayon fibers (1.7 dtex, staple length); and
(b) 60% round polypropylene fibers (1.7 dtex, staple length).

Sample 4 is a 55 gsm carded staple fiber nonwoven that was produced from a homogeneous blend of:
(a) 60% round viscose rayon fibers (1.7 dtex, staple length); and
(b) 40% round polypropylene fibers (1.7 dtex, staple length).

Sample 5 is a 50 gsm carded staple fiber nonwoven that was produced from a homogeneous blend of:
(a) 25% hollow, spiral polyethylene terephthalate fibers (10 dtex, staple length);
(b) 35% tri-lobal rayon fibers (3.3 dtex, staple length); and
(c) 40% round polypropylene fibers (1.7 dtex, staple length).

Sample 6 is a 55 gsm carded staple fiber nonwoven that was produced from a homogeneous blend of:
(a) 25% hollow, spiral polyethylene terephthalate fibers (10 dtex, staple length);
(b) 35% viscose rayon fibers (1.7 dtex, staple length); and
(c) 40% round polypropylene fibers (6.7 dtex, staple length).

Unless otherwise specified, all tests described herein were conducted on samples conditioned at a temperature of 73° F.±4° F. (about 23° C.±2.2° C.) and a relative humidity of 50%±4% for 2 hours prior to the test. As illustrated in the tables below, the example carded staple fiber nonwoven exhibited the following parameters.

TABLE 1

| Sample | 1 | 2 | 3 | 4 | 5 | 6 |
|---|---|---|---|---|---|---|
| Caliper (mm) | 0.99 | 1.17 | 0.73 | 0.67 | 0.80 | 0.79 |
| MD Flexural Rigidity (mN · cm) | 1.62 | 3.9 | 1.51 | 1.77 | 1.26 | 0.95 |
| CD Flexural Rigidity (mN · cm) | 0.17 | NA | 0.10 | 0.08 | 0.20 | 0.11 |

TABLE 1-continued

| Sample | 1 | 2 | 3 | 4 | 5 | 6 |
|---|---|---|---|---|---|---|
| Air Permeability (m³/m²/min) | 339 | NA | 174 | 166 | 243 | 280 |
| Pore Volume Ratio (mm³/μm · g/μm) | 10.26 | 9.48 | 14.14 | 11.02 | 8.77 | 9.30 |
| Pore Volume Radius Mode (μm) | 77.5 | 75 | 45 | 45 | 62.5 | 57.5 |

The following samples were tested with the samples obtained from the nonwoven rolls. Note that Sample 4 described above was not subsequently tested as the material was unavailable.

Sample 7 is a 43 gsm carded latex bonded nonwoven that was produced from a homogeneous blend of:
(a) 35% hollow, spiral polyethylene terephthalate fibers (10 dtex, staple length);
(b) 35% round polyethylene terephthalate fibers (6.7 dtex, staple length); and
(c) 30% latex.

Sample 8 is a 60 gsm carded latex bonded nonwoven that was produced from a homogeneous blend of:
(a) 35% hollow, spiral polyethylene terephthalate fibers (10 dtex, staple length);
(b) 35% round polyethylene terephthalate fibers (6 dtex, staple length); and
(c) 30% latex.

TABLE 2

| Sample | 1 | 2 | 3 | 5 | 6 | 7 | 8 |
|---|---|---|---|---|---|---|---|
| MD Bending Length (cm) | 2.57 | 3.28 | 2.24 | 2.84 | 2.36 | 5.27 | n/a |
| MD Flexural Rigidity (mN · cm) | 0.95 | 2.95 | 0.59 | 1.10 | 0.71 | 5.86 | n/a |
| CD Bending Length (cm) | 1.54 | 1.41 | 0.86 | 1.19 | 1.60 | 2.15 | n/a |
| CD Flexural Rigidity (mN · cm) | 0.21 | 0.24 | 0.03 | 0.08 | 0.23 | 0.41 | n/a |
| CD/MD Flexural Rigidity Ratio (%) | 22.1 | 8.1 | 5.2 | 7.3 | 32.4 | 7.0 | n/a |
| Caliper (mm) | 0.85 | 0.99 | 0.44 | 0.51 | 0.74 | 0.967 | 1.06 |
| Air Permeability (m³/m²/min) | 247 | 161 | 91 | 162 | 205 | n/a | 399 |
| Pore Volume Ratio (mm³/μm · g/μm) | 8.7 | 11.2 | 14.2 | 9.0 | 9.5 | 4.6 | 3.2 |
| Pore Volume Radius Mode (μm) | 90 | 80 | 40 | 60 | 80 | 160 | 153.3 |
| Pore Volume Factor (mm³/μm · g) | 782 | 895 | 568 | 542 | 760 | 742 | 486 |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

The invention claimed is:

1. A carded staple fiber nonwoven having a basis weight of between about 40 grams per square meter (gsm) and about 150 gsm, the carded staple fiber nonwoven comprising a blend of absorbing fibers, stiffening fibers and filler fibers, wherein the carded staple fiber nonwoven is non-heat stiffened, has an air permeability of between about 100 m³/m²/min and about 500 m³/m²/min, and a pore volume radius mode of between about 60 μm and about 120 μm, wherein the stiffening fibers form about 10% to about 50%, by weight, of the carded staple fiber nonwoven, wherein the absorbing fibers form about 10% to about 50%, by weight, of the carded staple fiber nonwoven, and wherein the filler fibers form about 60% or less, by weight, of the carded staple fiber nonwoven.

2. The carded staple fiber nonwoven of claim 1, wherein the carded staple fiber nonwoven has a caliper of between about 0.08 mm and about 0.20 mm per 10 gsm of basis weight.

3. The carded staple fiber nonwoven of claim 1, wherein the carded staple fiber nonwoven has a caliper of between about 0.5 mm to about 3 mm.

4. The carded staple fiber nonwoven of claim 1, wherein the carded staple fiber nonwoven has a basis weight of between about 45 gsm to about 85 gsm.

5. The carded staple fiber nonwoven of claim 1, wherein the carded staple fiber nonwoven has an MD flexural rigidity of less than about 4.8 mNcm.

6. The carded staple fiber nonwoven of claim 1, wherein the carded staple fiber nonwoven has a pore volume ratio of greater than about 8.

7. The carded staple fiber nonwoven of claim 1, wherein the stiffening fibers comprise hollow, spiral fibers formed from polyethylene terephthalate (PET), wherein the stiffening fibers have a linear density of between about 6 dtex and about 15 dtex.

8. The carded staple fiber nonwoven of claim 1, wherein the absorbing fibers comprise tri-lobal fibers formed from rayon, wherein the absorbing fibers have a linear density of between about 2 dtex and about 6 dtex.

9. The carded staple fiber nonwoven of claim 1, wherein the filler fibers comprise solid, round fibers formed from polypropylene (PP), wherein the filler fibers have a linear density of about 3 dtex or greater.

10. A carded staple fiber nonwoven, comprising:
a) about 10% to about 50%, by weight, of stiffening fibers comprising hollow, spiral fibers formed from polyethylene terephthalate (PET), wherein the stiffening fibers have a linear density of between about 6 dtex and about 15 dtex;
b) about 10% to about 50%, by weight, of absorbing fibers comprising tri-lobal fibers formed from rayon, wherein the absorbing fibers have a linear density of between about 2 dtex and about 6 dtex; and
c) about 1% to about 60%, by weight, of filler fibers comprising solid, round fibers formed from polypropylene (PP), wherein the filler fibers have a linear density of about 3 dtex or greater;
wherein the carded staple fiber nonwoven has a basis weight of between about 40 grams per square meter (gsm) and about 150 gsm, is non-heat stiffened, has an air permeability of between about 100 $m^3/m^2$/min and about 500 $m^3/m^2$/min, and a pore radius mode of between about 60 μm and about 120 μm.

11. The carded staple fiber nonwoven of claim 10, comprising:
about 20% to about 30%, by weight, of the stiffening fibers;
about 30% to about 40%, by weight, of the absorbing fibers; and
about 1% to about 50%, by weight, of the filler fibers.

12. The carded staple fiber nonwoven of claim 11, comprising:
about 25%, by weight, of the stiffening fibers;
about 35%, by weight, of the absorbing fibers; and
about 40%, by weight, of the filler fibers.

13. The carded staple fiber nonwoven of claim 10, wherein the carded staple fiber nonwoven has a caliper of between about 0.9 mm and about 1.2 mm, a basis weight of between about 45 gsm and about 85 gsm, and a density of between about 0.065 g/cc and about 0.094 g/cc.

14. An absorbent article, comprising:
a topsheet;
an absorbent core; and
a secondary topsheet positioned between the topsheet and the absorbent core,
wherein the secondary topsheet comprises the carded staple fiber nonwoven of claim 10.

15. The absorbent article of claim 14, wherein the secondary topsheet is bonded to the topsheet.

16. The carded staple fiber nonwoven of claim 1, wherein the carded staple fiber nonwoven web has a pore volume factor greater than 500.

17. A carded staple fiber nonwoven, comprising:
a) about 15% to about 35%, by weight, of stiffening fibers comprising hollow, spiral fibers formed from polyethylene terephthalate (PET), wherein the stiffening fibers have a linear density of between about 6 dtex and about 15 dtex;
b) about 10% to about 50%, by weight, of absorbing fibers comprising tri-lobal fibers formed from rayon, wherein the absorbing fibers have a linear density of between about 2 dtex and about 6 dtex; and
c) about 1% to about 60%, by weight, of filler fibers comprising solid, round fibers formed from polypropylene (PP), wherein the filler fibers have a linear density of about 3 dtex or greater;
wherein the carded staple fiber nonwoven has a basis weight of between about 40 grams per square meter (gsm) and about 150 gsm, is non-heat stiffened, has an air permeability of between about 100 $m^3/m^2$/min and about 500 $m^3/m^2$/min, and a pore volume radius mode of between about 60 μm and about 120 μm.

* * * * *